(12) United States Patent
Drozdzak et al.

(10) Patent No.: US 8,338,613 B2
(45) Date of Patent: Dec. 25, 2012

(54) PROCESS FOR THE PREPARATION OF BIDENTATE SCHIFF BASE RUTHENIUM CATALYSTS CONTAINING A SALICYLALDIMINE-TYPE LIGAND

(75) Inventors: Renata Drozdzak, Halluin (FR); Naoki Nishioka, Okayama (JP)

(73) Assignee: RIMTEC Corporation, Tokyo (JP)

( * ) Notice: Subject to any disclaimer, the term of this patent is extended or adjusted under 35 U.S.C. 154(b) by 506 days.

(21) Appl. No.: 12/586,115

(22) Filed: Sep. 17, 2009

(65) Prior Publication Data

US 2011/0065925 A1   Mar. 17, 2011

(51) Int. Cl.
*C07F 15/00* (2006.01)
(52) U.S. Cl. ........................................ 548/103
(58) Field of Classification Search ............ 548/103
See application file for complete search history.

(56) References Cited

OTHER PUBLICATIONS

Allaert et al. "Synthesis and activity for ROMP of bidentate Schiff base substituted second generation Grubbs catalysts" Journal of Molecular Catalysis: A Chemical, 2006, vol. 260, pp. 221-226.*
Occhipinti et al. "Green and Efficient Synthesis of Bidentate Schiff Base Ru Catalysts for Olefin Metathesis" Journal of Organic Chemistry, 2007, vol. 72, pp. 3561-3564.*
S. Chang et al., "Synthesis and Characterization of New Ruthenium-Based Olefin Metathesis Catalysts Coordinated with Bidentate Schiff-Base Ligands", *Organometallics*, 17(16), pp. 3460-3465 (1998).
O. Occhipinti et al., "Green and Efficient Synthesis of Bidentate Schiff Base Ru Catalysts for Olefin Metathesis", *J. Org. Chem.*, vol. 72, pp. 3561-3564 (2007).
B. Allaert et al., "Synthesis and activity for ROMP of bidentate Schiff base substituted second generation Grubbs catalysts", *Journal of Molecular Catalysis A: Chemical*, vol. 260, pp. 221-226 (2006).

* cited by examiner

*Primary Examiner* — Joseph Kosack
(74) *Attorney, Agent, or Firm* — Edwards Wildman Palmer LLP; Peter F. Corless; Christine C. O'Day (57) ABSTRACT

The invention relates to a process for the preparation of bidentate Schiff base catalysts containing a salicylaldimine-type ligand.

13 Claims, 6 Drawing Sheets

2:

a  $R^1$ = H, $R^2$ = 2,6-$i$-PrC$_6$H$_3$
b  $R^1$ = 4-NO$_2$, $R^2$ = 2,6-$i$-PrC$_6$H$_3$
c  $R^1$ = 4-NO$_2$, $R^2$ = 2,6-Me-4-MeOC$_6$H$_2$
d  $R^1$ = 4-NO$_2$, $R^2$ = 2,6-Me-4-BrC$_6$H$_2$
e  $R^1$ = 4-NO$_2$, $R^2$ = 2,6-Cl-4-CF$_3$C$_6$H$_2$
f  $R^1$ = 6-Me-4-NO$_2$, $R^2$ = 2,6-$i$-PrC$_6$H$_3$
g  $R^1$ = 4-NO$_2$, $R^2$ = 2,6-$i$-Pr-4-NO$_2$-C$_6$H$_3$
h  $R^1$ = 4-NO$_2$, $R^2$ = (1-adamantylmethyl)

Scheme 1

Scheme 2

FIG. 3

Scheme 4

FIG. 4 Scheme 5

FIG. 5

Scheme 6

FIG. 6

PROCESS FOR THE PREPARATION OF BIDENTATE SCHIFF BASE RUTHENIUM CATALYSTS CONTAINING A SALICYLALDIMINE-TYPE LIGAND

FIELD OF THE INVENTION

The present invention relates to a process for the preparation of bidentate Schiff base ruthenium catalysts containing a salicylaldimine-type ligand.

BACKGROUND OF THE INVENTION

Figure 1:
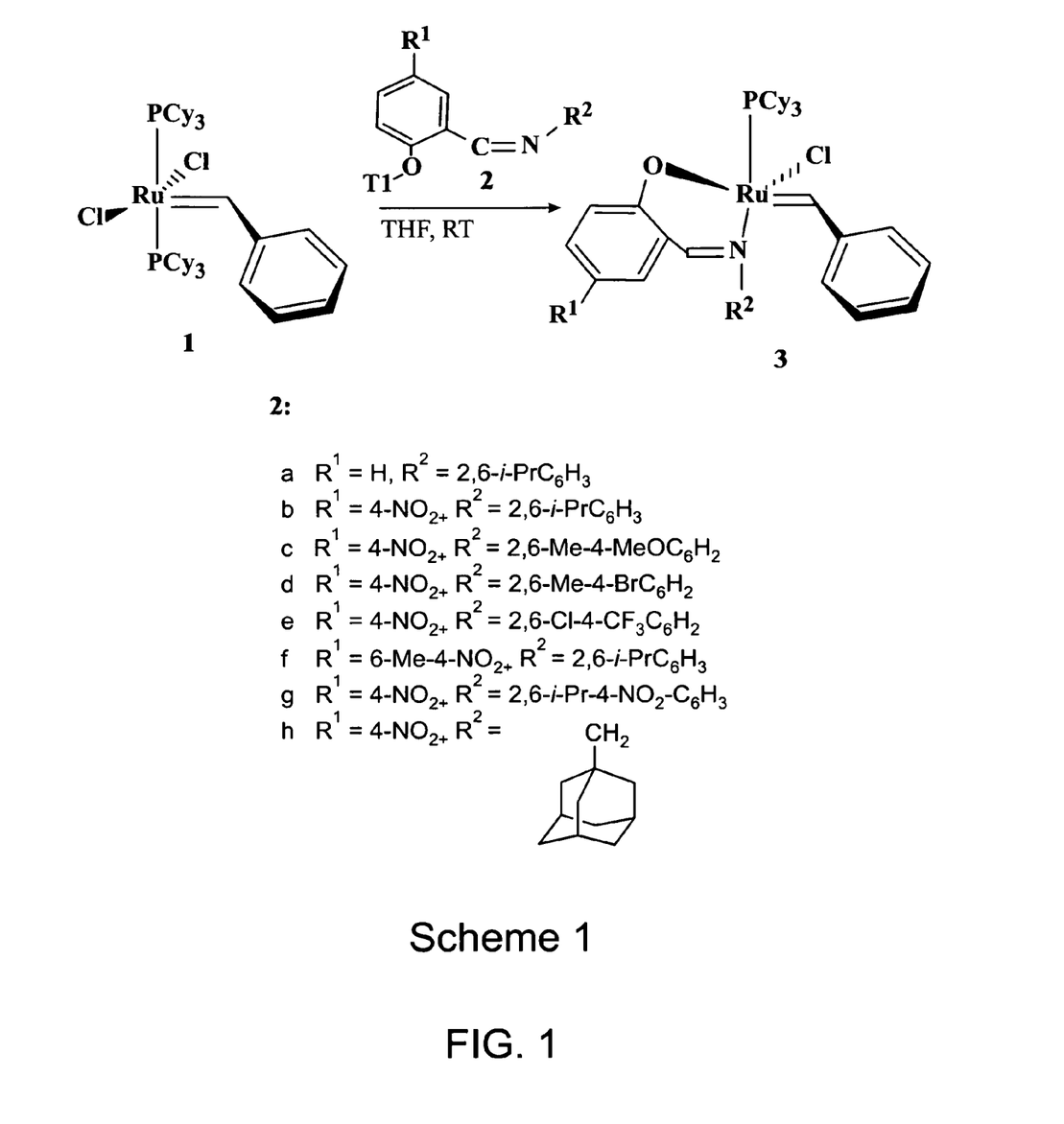
FIG. 1 is a scheme (Scheme 1) which summarizes the synthetic protocol for the bidentate Schiff base Ru catalysts disclosed by Grubbs and co-workers using thallium(I) as a counter ion for salicylaldimines.

During recent years, olefin metathesis has seen extraordinary development and has turned out to be a very versatile and efficient tool in organic synthesis. Ruthenium-based catalysts have become the first-choice catalysts for organic synthesis. During recent years, a huge effort has been dedicated to further develop and improve the characteristics of the Grubbs-type ruthenium catalysts. In this context, in 1998, Grubbs and co-workers disclosed a class of ruthenium-based catalyst for olefin metathesis involving bidentate Schiff base ligands 3. The synthetic protocol for the bidentate Schiff base Ru catalysts disclosed by Grubbs and co-workers, however, is saddled with a serious drawback, namely the use of a thallium (I) as counter ion for salicylaldimines (See Scheme 1 shown in FIG. 1) (S. Chang, LeRoy Jones II, Ch. Wang, L. M. Henling, R. H. Grubbs; *Organometallics* 1998, 17, 3460-3465).

Further improvement of Grubbs protocol has been given by Bjørsvik and co-workers, where the complexation with ruthenium was conducted by reacting one salicylaldimine ligand equivalent with 1 equiv of Grubbs first-generation catalyst (1) in presence of a 0.5 equiv of Ag$_2$CO$_3$ used as base (G. Occhipinti, V. R. Jensen, H. R. Bjørsvik, *J. Org. Chem.* 2007, 72, 3561-564). The complexation utilising the ligands containing nitro group provided a yield in the range 78-96%, which was as good as or better than the previously disclosed protocol.

The reaction utilising the ligand that lacks the electron-withdrawing p-nitro group, however, provided only a tiny yield, <2%. Attempts to improve the outcome of this reaction by prolonged reaction time and elevated temperature did not afford any significant improvements (a yield of only 4% was measured). It is believed that the major reason for the unsuccessful complexation was the relatively weak base (silver carbonate) that is used for the deprotonation of the phenolic group.

Figure 2:
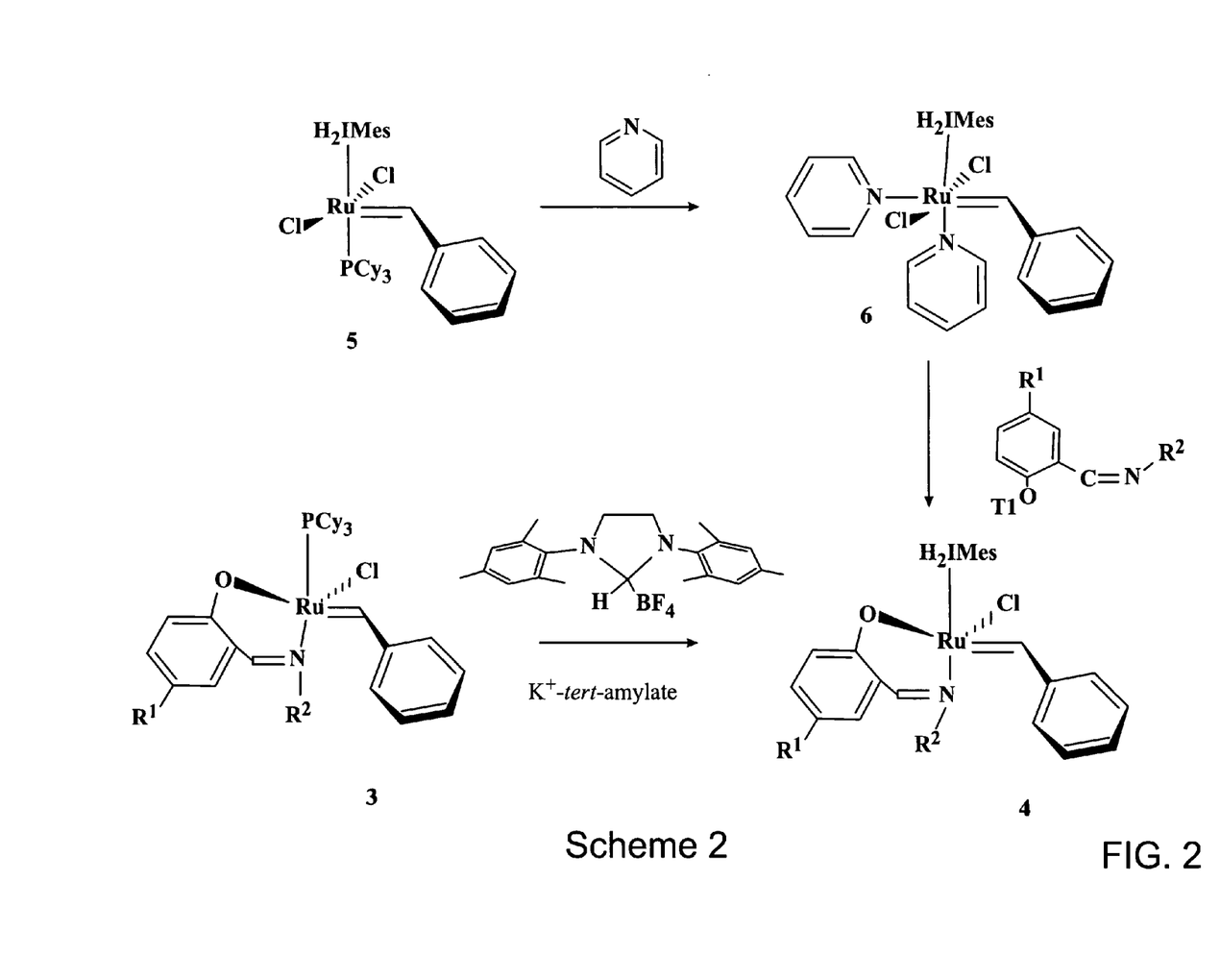
FIG. 2 is a scheme (Scheme 2) which summarizes the synthetic protocol which involves introducing salicylaldimine ligands to a complex already bearing the $H_2IMes$ ligand by Allaert et al. (J. Mol. Cat. A 2006, 260, 221-226).

Further efforts concerning the synthesis of NHC-salicylaldimine complexes concentrated on using the standard means for introducing the H$_2$IMes ligand, i.e., in situ formation of the free carbene from the imidazolinium salt with potassium tert-butoxide and subsequent reaction with the phosphine bearing ruthenium complex 3. Attempts to prepare complex 4 by this method resulted, however, in decomposition of the ruthenium benzylidene starting material. Faced with this roadblock, Verpoort et al. have chosen to approach 4 by introducing salicylaldimine ligands to a complex already bearing the H$_2$IMes ligand (B. Allaert, N. Dieltiens, N. Ledoux, C. Vercaemst, P. Van Der Voort, Ch. V. Stevens, A. Linden, F. Verpoort, *J. Mol. Cat. A:* 2006, 260, 221-226). Alkoxide and aryloxide ligands, as well as neutral donors, react readily with bis(pyridine) precursor 6. The pyridine ligands in 6 are far more labile than the phosphine ligand in 5 and are displaced easily by incoming Schiff base ligand, especially with the assistance of thallium ions. Accordingly, the thallium salts of salicylaldimine ligands 2 were prepared in situ with thallium ethoxide and reacted with 6 (See Scheme 2 shown in FIG. 2).

SUMMARY OF THE INVENTION

It is the object underlying the present invention to provide a short, efficient and environmentally benign alternative synthetic process for the preparation of bidentate Schiff base Ru catalysts.

The present invention provides a process for the preparation of a catalyst having the following formula:

(I)

wherein
X$_1$ denotes an anionic ligand;
L$_1$ is a neutral electron donor ligand;
R' and R" are each independently hydrogen or a radical selected from the group consisting of C$_{1-20}$ alkyl, C$_{2-20}$ alkenyl, C$_{2-20}$ alkynyl, C$_{1-20}$ carboxylate, C$_{1-20}$ alkoxy, C$_{2-20}$ alkenyloxy, C$_{2-20}$ alkynyloxy, aryl, aryloxy, C$_{1-20}$ alkoxycarbonyl, C$_{1-8}$ alkylthio, C$_{1-20}$ alkylsulfonyl, C$_{1-20}$ alkylsulfinyl, C$_{1-20}$ alkylsulfonate, arylsulfonate, C$_{1-20}$ alkylphosphonate, arylphosphonate, C$_{1-20}$ alkylammonium and arylammonium, optionally substituted with one or more moieties selected from the group consisting of C$_{1-10}$ alkyl, C$_{1-10}$ alkoxy, and aryl, or R' and R" may together form an aryl, arylidene, cycloalkyl or heteroaryl group, benzylidene being excluded. In a preferred embodiment, R' and R" together form a [3-phenyl-1H-inden-1-ylidene] moiety.

The [3-phenyl-1H-inden-1-ylidene] moiety may hereinafter also be referred to as "phenylindenylidene moiety", and the [1H-inden-1-ylidene] residue may also be referred to as "indenylidene" group.

S$_1$ to S$_4$ may be the same or different and are defined as for the compound of formula (III) shown below;
A is heteroaryl, substituted or unsubstituted alkyl, heteroalkyl or cycloalkyl,
B is hydrogen, C$_1$-C$_{20}$ alkyl, C$_1$-C$_{20}$ heteroalkyl aryl or heteroaryl, wherein each non-hydrogen group may be optionally substituted with one or more moieties selected from the group consisting of C$_1$-C$_{10}$ alkyl and aryl;
R$_{o1}$, R$_{o2}$, R$_{m1}$, R$_{m2}$ and R$_p$ are each selected from the group consisting of hydrogen, C$_1$-C$_{20}$ alkyl, C$_1$-C$_{20}$ heteroalkyl, C$_1$-C$_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl, wherein $R_{o1}$, $R_{o2}$, $R_{m1}$, $R_{m2}$ and $R_p$ can be joined to form a fused cyclic aliphatic or aromatic ring optionally substituted with one or more moieties selected from the group consisting of hydrogen, $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl comprising the following steps according to variant A or B:

Variant A

(i) reacting a compound of the formula (II)

(II)

wherein $PL_1$ and $PL_2$ are the same or different and each denote a phosphine ligand, R' and R" are as defined above, and $X_1$ and $X_2$ may be the same or different and each denote an anionic ligand with a compound of the formula (III)

(III)

wherein A and B are as defined above and $S_1$ to $S_4$ are substituents which are selected such that the compound of the formula (III) has a $pK_a \geq 6.2$ in the presence of a weak base having a $pK_b$ in the range of 3.5-7.0 to obtain a compound of the formula (IV)

(IV)

wherein $PL_1$, $S_1$ to $S_4$, A, B, $X_1$, R' and R" are as defined above, (ii) reacting the compound of formula (IV) with a precursor of a non-phosphine neutral electron donor ligand to obtain catalyst (I) or

Variant B (i) reacting a compound of the formula (V)

(V)

wherein $PL_1$, $PL_2$, $X_1$, $X_2$, R' and R" are as defined above with a precursor of a non-phosphine ligand $L_1$ as defined above to obtain a compound of the formula (VI)

(VI)

wherein $L_1$, $PL_2$, $X_1$, $X_2$, R' and R" are as defined above and (ii) reacting the compound of formula (VI) with a compound of the formula (III)

(III)

wherein $S_1$ to $S_4$, A and B are as defined above in the presence of a weak base having a $pK_b$ in the range of 3.5-7.0.

DETAILED DESCRIPTION OF THE INVENTION

The present invention is based on the surprising discovery that the successful complexation of the salicylaldimine ligand having a $pK_a \geqq 6.2$ with ruthenium is possible in the presence of a weak base such as $Ag_2CO_3$, for example, in order to prepare ruthenium catalysts of formula (I).

The NMR analysis of the reaction mixture obtained when carrying out the process according to the present invention shows that the complexation proceeds through several intermediate complexes which gradually disappear during the reaction, which has not been observed in any case for the benzylidene analogues. The complexation utilising $Ag_2CO_3$ as a weak base, for example, provides excellent yields in the range of 90-98%, which is highly superior to the yield obtained using thallium(I) salts.

Figure 3:
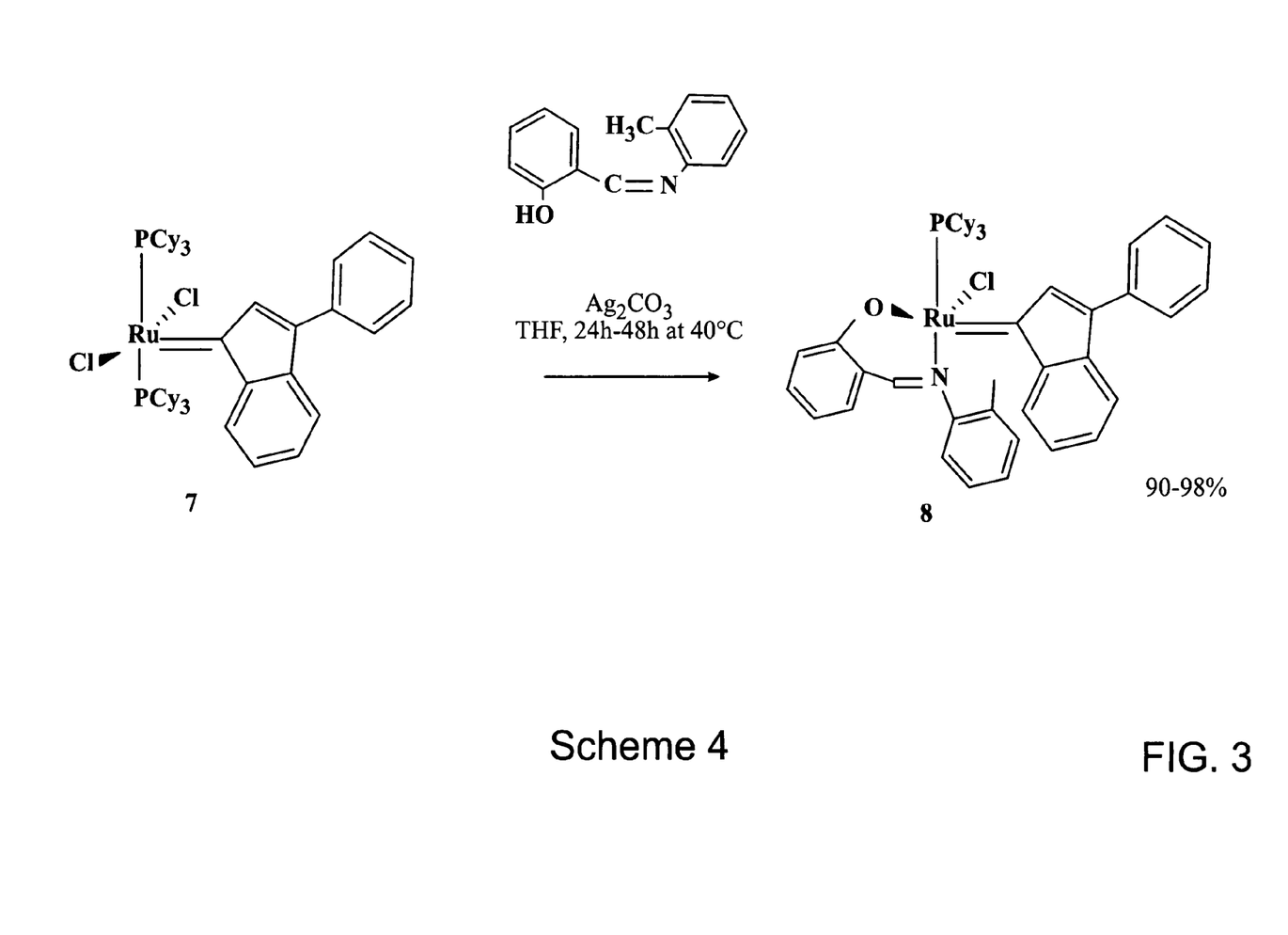
FIG. 3 is a scheme (Scheme 4) which shows complexation of the salicylaldimine ligand with ruthenium according to the present invention using $Ag_2CO_3$ as a weak base, thus providing excellent yields.

This is shown in an exemplary manner in Scheme 4 (FIG. 3).

The process according to the present invention can be carried out in two ways:

In the first variant (variant A), a compound of the formula (II)

is reacted with a compound of the formula (III)

in the presence of a weak base to obtain a compound of the formula (IV)

This step is exemplified in Scheme 4 above.

In the next step of variant A, the phosphine ligand in the compound of the formula (8) is replaced by a non-phosphine neutral electron donor ligand such as a sterically more complex N-heterocyclic ligand e.g. SIMes or IMes ligand.

According to variant (B) of the process according to the present invention, the replacement of the phosphine ligand with a non-phosphine ligand $L_1$ occurs already in the first step. Thus, according to variant (B), a compound of the formula (V)

is reacted with a precursor of a non-phosphine ligand $L_1$ first to obtain a compound of the formula (VI)

and the salicylaldimine ligand of the formula (III)

is only introduced in the next step in the presence of the weak base, such as $Ag_2CO_3$, for example, to prepare the desired bidentate Schiff base ruthenium catalyst.

In variant A, the replacement of the strong σ-donating phosphine ligand by a sterically more complex non-phosphine ligand such as a N-Heterocyclic ligand, e.g. SIMes ligand can surprisingly be achieved.

The in situ methods for preparation of SIMes containing ruthenium catalysts, in which all ingredients, that is, a SIMes ligand precursor, such as complex 7, for example, and a strong base are mixed together in an appropriate solvent (THF, benzene, toluene or hexane) lead to undesired results, such as diminished yields and formation of significant amounts of by-products. At least one of the contaminants is a ruthenium hydride or alkoxide species, which may be responsible for various side reactions. Treatment of 2 equiv of SIMes-Cl and 2 equiv of LiHMDS in toluene at 40° C. leads first to the formation of a second generation of indenylidene catalyst, bearing the $PCy_3$ moiety, which can be explained by ligand metathesis leading to bis-chloride-Ruthenium complex and decoordination of imine salt. The "base free" methods involving the use of SIMes adducts such as: chloroform adduct, $CO_2SIMes$, $Ag(SIMes)Cl$, which requires higher temperature (80° C.), fail due to low thermal stability of complex 8.

Figure 4:
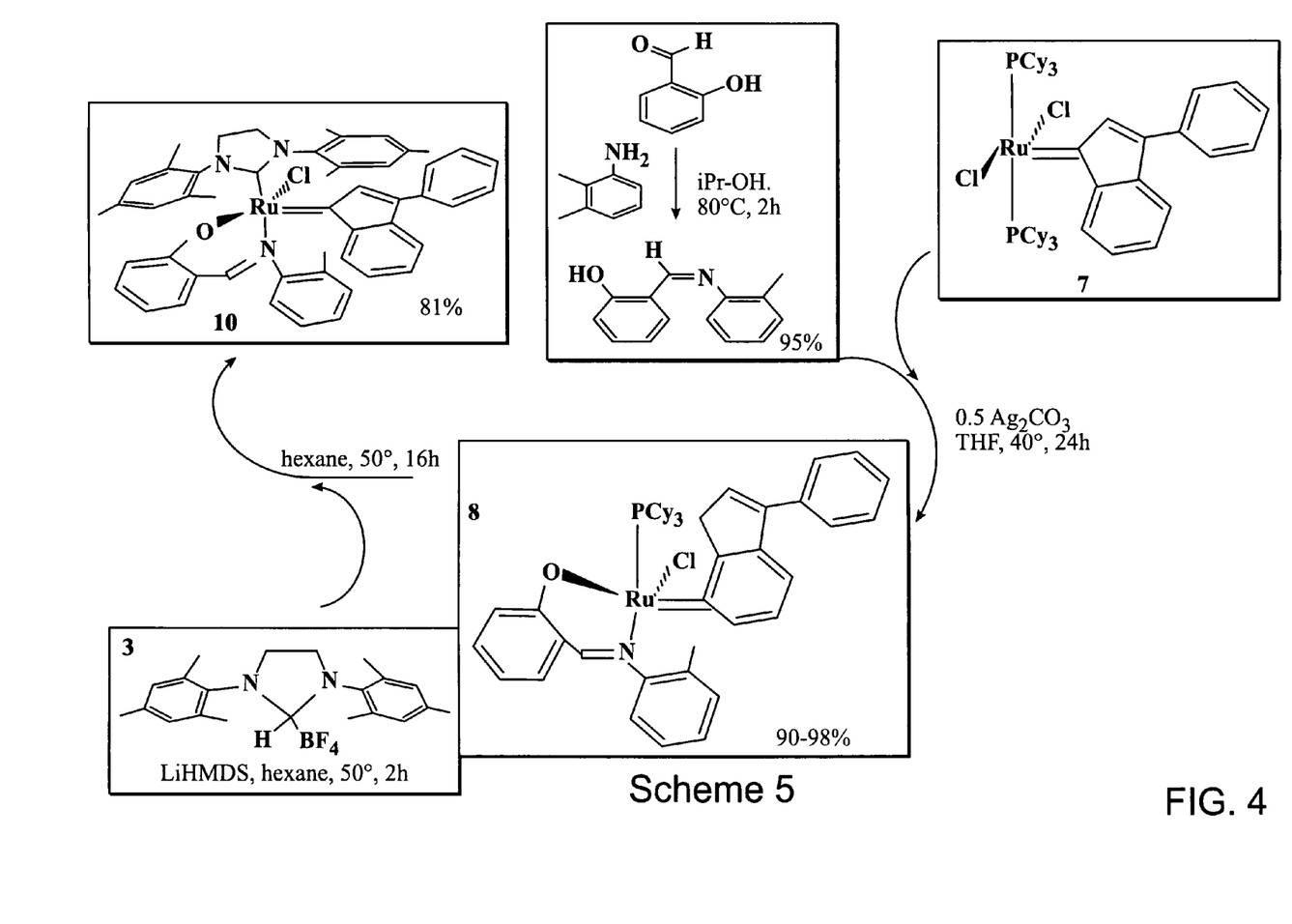
FIG. 4 is a scheme (Scheme 5) which exemplifies the process of the present invention which can be carried out as a good yielding quasi one-pot process.

However, according to the present invention, the complex 10, for example, can be obtained successfully by reaction of complex 8 with 3-4 equivalents of SIMes in hexane at 50° C., (Scheme 5 shown in FIG. 4). After the solvent is filtered off and remaining solid is washed several times with hexane, complex 10 can be isolated as a dark microcrystalline solid in 81% yield and with high purity.

Thus, the process according to the present invention can be carried out as a good yielding quasi-one pot process which is exemplified in Scheme 5 (here, R' and R" together form a phenylindenylidene moiety).

As the compounds used in the process according to the present invention are sensitive to air, moisture and impurities, it should be made sure that the starting material, the reagents and solvents used contain no impurities and are well dried. For example, in the reaction shown in Scheme 5 above, the quality of the SIMes-BF$_4$ salt is important to obtain the optimum results. Preferably, a salt is used which has been prepared according to the method by Hoveyda, recrystallised from ethanol (99.8%) and dried under vacuum.

Figure 5:
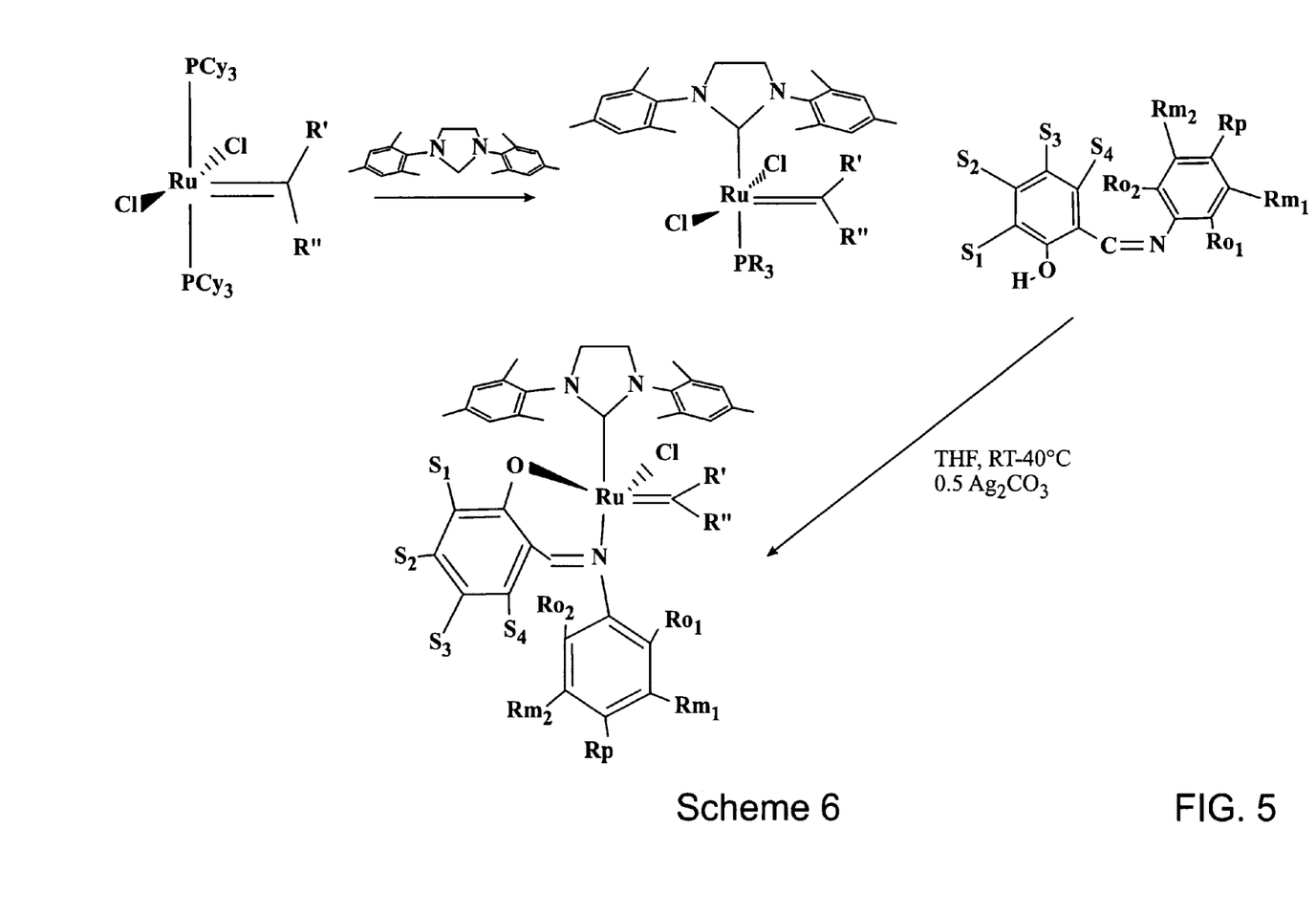
FIG. 5 is a scheme (Scheme 6) which exemplifies Variant (B) of the process according to the present invention, which does not require the synthesis of a pyridine complex, nor any further purification.

Variant (B) of the process according to the present invention is exemplified in Scheme 6 shown in FIG. 5. The first step is the substitution of one phosphine ligand by free SIMes, resulting in a mixed complex 11. The second step comprises the coordination of the salicylaldimine ligand by substituting the remaining phosphine ligand and one of the two chloro ligands. Noteworthy this protocol does not require the synthesis of a pyridine complex, nor any further purification. This procedure is highly superior compared to the previously described one using a NHC-pyridine complex and a thallium salt.

As mentioned above, one of the key features of the process according to the present invention is the successful complexation of ruthenium with the salicylaldimine ligand having a $pK_a \geq 6.2$ in the presence of a weak base.

As used herein, the terms below have the meanings indicated.

The parameter $pK_a$ is based on the so-called acid dissociation constant (denoted $K_a$) which is the equilibrium constant for the dissociation of a weak acid. According to the Brønsted-Lewis theory of acids and bases, an acid is a proton donor (HA, where H represents an acidic hydrogen atom), and a base is a proton acceptor. In aqueous solution, water can function as a base, as in the following general example.

$$HA + H_2O \rightleftharpoons A^- + H_3O^+$$

Acid dissociation constants are also known as the acidity constant or the acid-ionization constant. The term is also used for $pK_a$, which is equal to the negative decimal logarithm of $K_a$ (cologarithm of $K_a$).

In the present invention, the $pK_a$ value is determined by using Advanced Chemistry Development (ACD/Labs) Software, such as software V8.14 for Solaris referenced in J. Org. Chem. 2007, 72, 3561-3564.

The ACD/pK$_a$ DB software uses Hammett equations derived from a library of compounds to calculate the aqueous pK$_a$. In addition, two reference databases are available—one contains >31,000 experimental pK$_a$ values for approximately 16,000 compounds in aqueous solutions; the other provides experimental data for more than 2000 molecules in non-aqueous solvents. This software is used by the majority of pharmaceutical and API companies worldwide, and has been tested on a broad variety of chemical classes.

The salicylaldimine ligand of formula (III) used in the present invention has a $pK_a \geq 6.2$ which is above the $pK_a$ of 5.81±0.30 mentioned by Bjørsvik in J. Org. Chem. 2007, 72, 3561-3564 for a complexation resulting in tiny yields (2%).

According to the present invention, a complexation can be achieved in high yields even when using salicylaldimine ligands having a $pK_a$ as high as 11.

The $pK_a$ of the salicylaldimine ligand is basically determined by the nature of the substituents $S_1$ to $S_4$. It is common general knowledge that electron-withdrawing groups (such as the nitro groups described in the above mentioned paper by Bjørsvik) will decrease the $pK_a$ of the phenolic group whereas electron-neutral (hydrogen) or electron-donating groups will increase the $pK_a$.

Suitable electron-donating groups are known to the skilled person and include substituted or unsubstituted amino, mono- and dialkylamino, $C_1$-$C_{20}$ alkoxy, $C_1$-$C_{20}$ alkyl, thioalkyl, aryl, aryloxy and the like.

Examples include methoxy, methyl, isopropyl, t-butyl and dimethylamino.

On the basis of these lists of electron-neutral/-donating groups, the skilled person can easily conceive compounds of formula (III) having a $pK_a \geq 6.2$.

The presence of electron-withdrawing groups is not excluded provided that the corresponding phenols have a $pK_a \geq 6.2$. For example, such electron-withdrawing groups include ammonium, nitro halogen, such as bromo, chloro, fluoro, iodo and the like.

The following Table 1 lists pK$_a$ values for various phenolic Schiff base ligand compounds:

TABLE 1

| | Phenolic part | | | | Aniline part | | | | | |
|---|---|---|---|---|---|---|---|---|---|---|
| No. | $S^1$ | $S^2$ | $S^3$ | $S^4$ | $R_{o1}$ | $R_{o2}$ | $R_{m1}$ | $R_{m2}$ | $R_p$ | pKa |
| | | | | pKa 7.22-11.08 | | | | | | |
| 1 | H | H | tbPhO$^{3*}$ | H | —CH$_3$ | H | H | H | H | 8.95 |
| 2 | H | H | Pyr$^{2*}$ | H | —CH$_3$ | H | H | H | H | 9.51 |
| 3 | H | H | py$^{4*}$ | H | H | H | H | H | H | 7.14 |
| 4 | H | H | Pip$^{1*}$ | H | —CH$_3$ | H | H | H | H | 11.08 |
| 5 | H | Pip$^{1*}$ | H | Pip$^{1*}$ | —CH$_3$ | H | H | H | H | 9.55 |
| 6 | H | Pip$^{1*}$ | H | H | —CH$_3$ | H | H | H | H | 9.17 |
| 7 | Pip$^{1*}$ | H | H | H | —CH$_3$ | H | H | H | H | 10.05 |
| 8 | —OCH$_3$ | H | —OCH$_3$ | H | —CH$_3$ | —CH$_3$ | H | H | H | 9.25 |
| 9 | —OCH$_3$ | H | —OCH$_3$ | H | —CH$_3$ | H | H | H | H | 9.24 |
| 10 | —OCH$_3$ | H | —OCH$_3$ | H | —CH$_3$ | —CH$_3$ | H | H | —CH$_3$ | 9.32 |
| 11 | —OCH$_3$ | H | —OCH$_3$ | OCH$_3$ | —CH$_3$ | —CH$_3$ | H | H | —CH$_3$ | 8.93 |
| 12 | H | H | H | H | —OCH$_3$ | H | H | H | H | 8.87 |
| 13 | H | H | H | H | —CH$_3$ | —CH$_3$ | H | H | H | 8.85 |
| 14 | H | H | H | H | —Cl | H | H | H | H | 8.58 |
| 15 | H | H | H | H | —CH$_3$ | —CH$_3$ | H | H | —CH$_3$ | 8.84 |
| 16 | H | H | H | H | —CH$_3$ | —CH$_3$ | H | H | —Br | 8.69 |
| 17 | H | H | H | H | —$^i$Pr | —$^i$Pr | H | H | H | 8.83 |
| 18 | H | H | H | H | H | H | H | H | —$^t$But | 8.92 |
| 19 | H | H | H | H | H | H | H | H | H | 8.47 |
| 20 | H | H | H | H | H | H | H | H | —$^t$But | 8.92 |

TABLE 1-continued

| | Phenolic part | | | | Aniline part | | | | | |
|---|---|---|---|---|---|---|---|---|---|---|
| No. | S¹ | S² | S³ | S⁴ | $R_{o1}$ | $R_{o2}$ | $R_{m1}$ | $R_{m2}$ | $R_p$ | pKa |
| 21 | H | H | H | H | H | H | —Br | H | H | 8.76 |
| 22 | H | H | H | H | —CH₃ | H | H | H | H | 8.93 |
| 23 | H | H | H | H | —ᵗBut | —ᵗBut | H | H | —ᵗBut | 8.93 |
| 24 | H | H | H | H | H | H | H | H | H | 8.47 |
| 25 | H | H | —OCH₃ | H | —CH₃ | H | H | H | H | 9.24 |
| 26 | H | H | —OCH₃ | H | H | H | H | H | —ᵗBut | 9.32 |
| 27 | H | H | —OCH₃ | H | —CH₃ | —CH₃ | H | H | —CH₃ | 9.33 |
| 28 | H | H | —OCH₃ | H | —CH₃ | —CH₃ | H | H | H | 9.25 |
| 29 | H | —OCH₃ | H | H | —CH₃ | H | H | H | H | 8.38 |
| 30 | H | —OCH₃ | H | H | —ᵗBut | —ᵗBut | H | H | —ᵗBut | 8.47 |
| 31 | H | —OCH₃ | H | H | H | H | H | H | —ᵗBut | 8.45 |
| 32 | H | —OCH₃ | H | OCH₃ | H | H | H | H | —ᵗBut | 8.05 |
| 33 | H | —OCH₃ | H | H | —CH₃ | —CH₃ | H | H | H | 8.39 |
| 34 | H | —OCH₃ | H | H | —CH₃ | —CH₃ | H | H | —CH₃ | 8.46 |
| 35 | H | —OCH₃ | H | H | Cl | H | H | H | H | 8.12 |
| 36 | H | —OCH₃ | H | H | Cl | H | H | H | —OCH₃ | 8.47 |
| 37 | H | —OCH₃ | H | OCH₃ | —CH₃ | —CH₃ | H | H | —CH₃ | 8.06 |
| 38 | H | —SCH₃ | H | H | —CH₃ | H | H | H | H | 8.27 |
| 39 | H | —SCH₃ | H | —SCH₃ | —CH₃ | H | H | H | H | 7.75 |
| 40 | H | NH₂ | H | H | —CH₃ | H | H | H | H | 8.81 |
| 41 | H | NH₂ | H | NH₂ | —CH₃ | H | H | H | H | 8.83 |
| 42 | H | NH₂ | H | NH₂ | H | H | H | H | —CH₃ | 8.91 |
| 43 | OCH₃ | H | H | H | —CH₃ | —CH₃ | H | H | H | 8.77 |
| 44 | H | —Br | H | H | H | H | H | H | H | 7.37 |
| 45 | H | —Br | H | H | —CH₃ | H | H | H | H | 7.79 |
| 46 | H | —Br | H | —Br | —CH₃ | H | H | H | H | 6.80 |
| 47 | H | H | H | H | H | H | —Cl | H | H | 8.67 |
| 48 | —Br | H | H | H | —CH₃ | H | H | H | H | 7.22 |
| 49 | H | H | —Cl | H | —CH₃ | H | H | H | H | 8.87 |
| 50 | H | —Cl | -Cy | H | H | H | H | H | —CH₃ | 7.58 |
| 51 | H | —Cl | -Cy | H | —CH₃ | H | H | H | H | 7.51 |
| 52 | H | H | —Br | H | —CH₃ | H | H | H | H | 8.19 |
| 53 | H | H | —F | H | —CH₃ | H | H | H | H | 8.77 |
| 54 | —ᵗBut | H | —ᵗBut | H | —CH₃ | H | H | H | H | 10.34 |
| 55 | —ᵗBut | H | —ᵗBut | H | —CH₃ | —CH₃ | H | H | —CH₃ | 10.42 |
| 56 | —ᵗBut | H | —ᵗBut | H | —ᵗBut | —ᵗBut | H | H | —ᵗBut | 10.43 |
| 57 | —ᵗBut | H | —ᵗBut | —ᵗBut | H | H | H | H | —CH₃ | 10.53 |
| 58 | —ᵗBut | H | Cy | H | —CH₃ | H | H | H | H | 10.36 |
| 59 | —ᵗBut | H | H | H | —CH₃ | —CH₃ | H | H | —CH₃ | 10.22 |
| 60 | —ᵗBut | H | H | Cl | —CH₃ | H | H | H | H | 9.14 |
| 61 | —ᵗBut | H | Cy | Cl | —CH₃ | H | H | H | H | 9.39 |
| 62 | H | —ᵗBut | H | H | —CH₃ | H | H | H | H | 8.86 |
| 63 | H | —ᵗBut | H | H | —ᵗBut | —ᵗBut | H | H | —ᵗBut | 8.97 |
| 64 | H | —ᵗBut | H | H | —CH₃ | —CH₃ | H | H | —CH₃ | 8.97 |
| 65 | H | —ᵗBut | H | H | H | H | H | H | —ᵗBut | 8.95 |
| 66 | H | —ᵗBut | H | —ᵗBut | H | H | H | H | —CH₃ | 9.05 |
| 67 | H | H | —N(CH₃)₂ | H | —CH₃ | H | H | H | H | 7.85 |
| 68 | H | H | —N(CH₃)₂ | H | —CH₃ | —CH₃ | H | H | H | 8.86 |
| 69 | H | N(CH₃)₂ | H | H | —CH₃ | H | H | H | H | 8.86 |
| 48 | H | N(CH₃)₂ | H | H | —CH₃ | —CH₃ | H | H | H | 8.86 |
| 70 | H | N(CH₃)₃ | H | H | —CH₃ | H | H | H | H | 6.64 |
| 71 | H | N(CH₃)₂ | H | H | Ipr | Ipr | H | H | H | 8.84 |
| 72 | H | H | —OCF₃ | H | —CH₃ | H | H | H | H | 8.14 |
| 73 | H | H | —CF₃ | H | —CH₃ | H | H | H | H | 7.36 |
| 74 | H | —CF₃ | H | H | —CH₃ | H | H | H | H | 7.75 |
| 75 | H | OPh | H | H | —CH₃ | H | H | H | H | 8.09 |
| 76 | H | OPh | H | OPh | —CH₃ | H | H | H | H | 7.39 |
| 91 | H | H | Ph | H | —CH₃ | —CH₃ | H | H | —CH₃ | 5.95 |
| 92 | H | Ph | H | H | —CH₃ | —CH₃ | H | H | —CH₃ | 8.53 |
| 93 | H | Ph | H | Ph | —CH₃ | H | H | H | H | 8.29 |
| 94 | Ph | H | Ph | H | —CH₃ | H | H | H | H | 8.68 |
| 95 | H | H | Ph | H | —CH₃ | —CH₃ | H | H | —CH₃ | 8.66 |
| pKa 6.36-6.95 | | | | | | | | | | |
| 96 | —Br | H | —Br | H | —CH₃ | H | H | H | H | 6.64 |
| 97 | —Cl | H | Cl | H | —CH₃ | H | H | H | H | 6.80 |
| 98 | H | H | H | —Br | —CH₃ | —CH₃ | H | H | —CH₃ | 6.89 |
| 99 | H | NO₂ | H | H | —CH₃ | —CH₃ | H | H | H | 6.95 |
| 100 | H | NO₂ | H | H | —CH₃ | H | H | H | H | 6.95 |
| 101 | H | NO₂ | H | H | Cl | H | H | H | H | 6.61 |
| 102 | H | NO₂ | H | H | —CH₃ | H | H | H | H | 7.04 |
| 103 | H | NO₂ | H | H | —CH₃ | H | H | H | H | 7.04 |
| 104 | H | NO₂ | H | H | H | H | H | H | NO₂ | 6.36 |

TABLE 1-continued

| | Phenolic part | | | | Aniline part | | | | | |
|---|---|---|---|---|---|---|---|---|---|---|
| No. | $S^1$ | $S^2$ | $S^3$ | $S^4$ | $R_{o1}$ | $R_{o2}$ | $R_{m1}$ | $R_{m2}$ | $R_p$ | pKa |
| 105 | —OCF$_3$ | H | H | H | —CH$_3$ | H | H | H | H | 6.88 |
| 106 | —CF$_3$ | H | H | H | —CH$_3$ | H | H | H | H | 6.77 |
| 107 | H | —CF$_3$ | H | —CF$_3$ | —CH$_3$ | H | H | H | H | 6.72 |
| | | | | | 4.89-5.95 | | | | | |
| 108 | H | NO$_2$ | H | NO$_2$ | —CH$_3$ | H | H | H | H | 5.42 |
| 109 | F | F | F | F | —CH$_3$ | H | H | H | H | 5.50 |
| 110 | Cl | Cl | Cl | Cl | —CH$_3$ | H | H | H | H | 4.89 |
| 111 | H | H | NO$_2$ | H | —$^t$But | —$^t$But | H | H | —$^t$But | 5.89 |
| 112 | H | H | NO$_2$ | H | —$^t$But | H | H | H | H | 5.82 |
| 113 | H | H | NO$_2$ | H | $^i$Pr | $^i$Pr | H | H | H | 5.81 |
| 114 | H | H | NO$_2$ | H | —CH$_3$ | —CH$_3$ | H | H | H | 5.83 |
| 115 | H | H | NO$_2$ | H | —CH$_3$ | H | H | H | H | 5.82 |
| 116 | H | H | NO$_2$ | H | —CH$_3$ | —CH$_3$ | H | H | | 5.72 |
| 117 | H | H | NO$_2$ | H | —CH$_3$ | —CH$_3$ | H | H | —CH$_3$ | 5.89 |
| 118 | H | H | NO$_2$ | H | —Cl | H | H | H | H | 5.63 |
| 119 | H | H | NO$_2$ | H | H | H | H | H | H | 5.55 |
| 120 | H | H | NO$_2$ | H | H | H | —Br | H | H | 5.77 |
| 121 | H | H | NO$_2$ | H | H | H | H | H | —Cl | 5.71 |
| 122 | H | H | NO$_2$ | H | H | H | H | H | —CH$_3$ | 5.88 |
| 123 | H | H | NO$_2$ | H | H | H | H | H | —$^t$But | 5.88 |
| 124 | H | H | NO$_2$ | H | H | H | H | H | —N(CH$_3$)$_2$ | 5.88 |

$^1$(Pip = Piperidinyl)
$^2$(Pyrl = 1-Pyrrolidino)
$^3$(tbPhO = 4-tert-Butylphenoxy)
$^4$(Py = 2-Pyridyl)
Entries No. 1 to 107 have a pK$_a \geq 6.2$ and hence are suitable for use in the present invention.
Entries No. 108 to 124 have a pK$_a$ lower than 6.2 and their use is not according to the invention.

It is worth noting that it was not possible to obtain bidentate Schiff base ruthenium catalysts when using the above phenolic compounds having a pK$_a$ lower than 6 in an attempt to prepare indenylidene type catalysts rather than the benzylidene type catalysts described by Bjørsvik. Apparently, the method disclosed by Bjørsvik is limited to the preparation of benzylidene type catalysts even when salicylaldimine ligands are used having a pK$_a$ in the range of 5.8.

On the other hand, according to the present invention, indenylidene type bidentate Schiff base ruthenium catalysts can be obtained in good yields using phenolic compounds of formula (III) having a pK$_a \geq 6.2$, preferably $\geq 7.2$, more preferably $\geq 7.5$, still more preferably $\geq 7.8$ and most preferably in the range of 8.4 to 10.3.

However, even compounds having a pK$_a$ as high as 12, 12.5, 13 or even 15 can successfully be used in the process according to the present invention.

Next, the pK$_b$ value will be explained:

A weak base is a base that does not ionize fully in an aqueous solution. As Bronsted-Lowry bases are proton acceptors, a weak base may also be defined as a base in which protonation is incomplete. This results in a relatively low pH value compared to strong bases. Bases have a pH in an aqueous solution of greater than 7 (7 is neutral, like pure water) to 14 (though some bases have pH values greater than 14). The pH value is defined as:

$$pH = -\log_{10}[H^+]$$

Since bases are proton acceptors, the base receives a hydrogen ion from water, H$_2$O, and the remaining H$^+$ concentration in the solution determines the pH value. Weak bases will cause a higher H$^+$ concentration because they are less protonated than stronger bases and, therefore, more hydrogen ions remain in the solution. If the H$^+$ concentration is increased in the formula, a low pH value results. However, the pH value of bases is usually calculated using the OH$^-$ concentration to find the pOH value first. This is done because the H$^+$ concentration is not a part of the reaction, while the OH$^-$ concentration is.

$$pOH = -\log_{10}[OH^-]$$

Since $K_w = [H_3O^+][OH^-]$ then, $K_a \times K_b = K_w$.

By taking logarithms of both sides of the equation, the following is reached:

$$\log K_a + \log K_b = \log K_w$$

Finally, multiplying throughout the equation by −1, the equation turns into:

$$pK_a + pK_b = pK_w = 14.00$$

After calculating the pOH from the above pOH formula, the pH value can be calculated using the formula $$pH = pK_w - pOH, \text{ wherein } pK_w = 14.00 \text{ at a temperature of } 25°\text{ C.}$$

The weak base used in the present invention is characterised by its pK$_b$ value as defined above. Suitable weak bases for use in the present invention have a pK$_b$ value in the range of 3.5 to 7.

For example, Ag$_2$CO$_3$ has a pK$_b$ value of 3.68 in water, wherein the following equilibrium is formed:

Examples of other suitable bases for use in the present invention include Li$_2$CO$_3$, Na$_2$CO$_3$, K$_2$CO$_3$ and CuCO$_3$. The pK$_b$ of these carbonates is about 3.69.

Further examples include carboxylates.

An anionic ligand (X$_1$, X$_2$) is any ligand which, when removed from a metal centre in its closed shell electron configuration, has a negative charge.

Suitable anionic ligand precursors include, but are not limited to, halides, carboxylic acids and/or their alkali metal or other salts, for example, sodium acetate, trifluoroacetate, beta-diketonates, acetylacetonate, propionate, butyrate, benzoate, or their corresponding acids; carboxylic acids and/or their alkali metal or other salts in a position alpha to a heteroaromatic nitrogen atom, such as, but not limited to, picolinic acid and substituted picolinic acids; picolinate and substituted picolinates, and their corresponding N-oxides. Suitable substituents for picolinic acid and picolinate include, but are not limited to, carboxylic acid, carboxylate, halogen, alkyl, heteroaryl, and aryl. Examples of beta-diketones (from which beta-diketonates are derived) include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, trifluoroacetylacetone, hexafluoroacetylacetone, benzoyltrifluoroacetone, pivaloyl-trifluoroacetone, heptafluorodimethyloctanedione, octafluorohexanedione, decafluoroheptanedione, 2-furoyltrifluoroacetone, 2-thionyltrifluoroacetone, 3-chloro-2,4-pentanedione, 3-ethyl-2,4-pentanedione, 3-methyl-2,4-pentanedione, methyl 4-acetyl-5-oxohexanoate. Preferably, $X_1$ and $X_2$ are the same and denote chlorine.

A neutral electron donor ($L_1$, $L_2$) is any non-phosphine ligand which, when removed from a metal centre in its closed shell electron configuration, has a neutral charge, i.e., is a Lewis base.

Examples of neutral electron donor ligands $L_1$ include ligands which are derived, for example, from unsubstituted or substituted heteroarenes such as furan, thiophene, pyrrole, pyridine, bipyridine, picolylimine, gamma-pyran, gamma-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole.

Particularly preferred neutral electron donors for use in the present invention include N-heterocyclic carbene (NHC) ligands. A wide range of NHC ligands are now commercially available. Suitable precursors of such neutral electron donor ligands include 1,3-diisopropylimidazolium tetrafluoroborate, 1,3-bis(1-adamantanyl)imidazolium tetrafluoroborate, 1,3-Bis-(tert-butyl)-4,5-dihydro-1H-imidazolium tetrafluoroborate, N,N'-(2,4,6-trimethyl)dihydroimidazolium chloride and N,N'-(2,6-diisopropylphenyl)dihydroimidazolium chloride, 1,3-bis(2,4,6-trimethylphenyl)-4,5-dihydroimidazolium tetrafluoroborate (SIMes.$BF_4$), 1,3-bis(2,4-dimethylphenyl)-4,5-dihydroimidazolium tetrafluoroborate (SIMe.$BF_4$); 1,3-bis(2-methylphenyl)-4,5-dihydroimidazolium tetrafluoroborate, 1,3-bis(2-butylphenyl)-4,5-dihydroimidazolium tetrafluoroborate, 1-methyl-3-(2,4,6-trimethylphenyl)-4,5-dihydroimidazolium tetrafluoroborate, 1-cyclohexyl-3-(2,4,6-trimethylphenyl)-4,5-dihydroimidazolium tetrafluoroborate, 1-octyl-3-(2,4,6-trimethylphenyl)-4,5-dihydroimidazolium tetrafluoroborate, 1-(1-adamantyl)-3-(2,4,6-trimethylphenyl)-4,5-dihydroimidazolium tetrafluoroborate.

Examples of phosphine ligands $PL_1$ and $PL_2$ include phosphines of the formula $PR_3R_4R_5$, where $R_3$, $R_4$ and $R_5$ are selected from $C_1$-$C_{10}$ primary alkyl, secondary alkyl or cycloalkyl, alkoxy aryl, aryloxy. $R_3$, $R_4$ and $R_5$ may be the same or different.

The term "aryl" includes a mono- and polyaromatic monovalent radical such as phenyl, benzyl, naphthyl, anthracenyl, adamantyl, phenantracyl, fluoranthenyl, chrysenyl, pyrenyl, biphenylyl, picenyl and the like, including fused benzo-$C_{5-8}$ cycloalkyl radicals such as, for instance, indanyl, 1,2,3,4-tetrahydronaphtalenyl, fluorenyl and the like.

The term "heteroaryl" includes a mono- and polyheteroaromatic monovalent radical including one or more heteroatoms each independently selected from the group consisting of nitrogen, oxygen, sulfur and phosphorus, such as for instance pyridyl, pyrazinyl, pyrimidinyl, pyridazinyl, triazinyl, triazolyl, imidazolyl, pyrazolyl, thiazolyl, isothiazolyl, oxazolyl, pyrrolyl, furyl, thienyl, indolyl, indazolyl, benzofuryl, benzothienyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, pyrazolinyl, pyrazolidinyl, pyrrolinyl, pyrrolidinyl and the like, including all possible isomeric forms thereof.

The term "cycloalkyl" includes a monocyclic aliphatic radical having from 3 to 8 carbon atoms, such as for instance cyclopropyl, cyclobutyl, methylcyclobutyl, cyclopentyl, methylcyclopentyl, cyclohexyl, methylcyclohexyl, cycloheptyl, cyclooctyl and the like, or a $C_{7-10}$ polycyclic aliphatic radical having from 7 to 10 carbon atoms such as, for instance, norbornyl or adamantyl.

As used herein, the term alkyl includes straight and branched chain saturated hydrocarbon monovalent radicals having from 1 to 6 carbon atoms such as, for example, methyl, ethyl, propyl, n-butyl, 1-methylethyl, 2-methylpropyl, 1,1-dimethylethyl, 2-methylbutyl, n-pentyl, dimethylpropyl, n-hexyl, 2-methylpentyl, 3-methylpentyl and the like, and the higher homologues thereof having 7 to 20 carbon atoms, such as for instance heptyl, ethylhexyl, octyl, nonyl, decyl, dodecyl, octadecyl and the like.

The term "heteroalkyl" denotes an alkyl group as defined above wherein one or more carbon atoms may be replaced by heteroatoms such as nitrogen, phosphorus, oxygen, sulfur and the like.

The term "heterocycloalkyl" denotes a cycloalkyl group as defined above wherein one or more carbon atoms may be replaced by heteroatoms such as nitrogen, phosphorus, oxygen, sulfur and the like.

Unless indicated otherwise, the term "substituted" refers to substituents selected from the group consisting of $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl.

According to a preferred embodiment of the invention, a catalytic quantity of silver(I) chloride is added to the reaction mixture.

The amount of weak base used is generally in the range of 1 to 2 equivalents relative to the amount of compound (III).

The starting metal complex, the Schiff base ligands, the weak base, such as $Ag_2CO_3$ and, optionally, silver(I) chloride are preferably pre-mixed and then a suitable solvent that does not react with any components of the mixture is added. In the present invention, aprotic solvents which do not possess any acidic protons having a dielectric constant above 3 are preferably used.

Generally, the dielectric constant of the solvent provides a rough measure of a solvent's polarity. Solvents with a dielectric constant of less than 15 are generally considered nonpolar. Technically, the dielectric constant measures the solvent's ability to reduce the field strength of the electric field surrounding a charged particle immersed in it. Examples are given in Table 2 below:

TABLE 2

| solvent | dielectric constant[1] |
|---|---|
| hexane | 1.89 at 20° C. |
| tetrahydrofuran | 7.52 at 25° C. |
| $CH_2Cl_2$ | 8.93 at 25° C. |
| acetone | 21.01 at 20° C. |
| chloroform | 4.81 at 20° C. |
| toluene | 2.38 at 23° C. |
| benzene | 2.28 at 23° C. |
| diethyl ether | 4.34 at 25° C. |

[1]Solvent Physical Properties. Sigma-Aldrich. Retrieved on 23 May 2007.

As mentioned above, the preferred solvent for use in the present invention has a dielectric constant above 3 and such solvents include tetrahydrofuran, $CH_2Cl_2$, chloroform and diethyl ether, with tetrahydrofuran being particularly preferred.

The reaction mixture is then heated and stirred. In general, the reaction is carried out at a temperature in the range of 20-60° C.

The reaction time is in general 2 to 72 h.

After the reaction has been completed, the reaction mixture is cooled to about 0° C. to remove any by-products formed such as $PCy_3AgCl$ by filtration.

Subsequently, the solvent is removed by evaporation, usually under reduced pressure.

The ratio of the compound of the formula (II) to the salicylaldimine ligand (III) used in step (i) of variant A is preferably equimolar.

The ratio of the compound of the formula (V) to the precursor of a non-phosphine ligand $L_1$ used in step (i) of variant B is preferably about 1-3 equivalents.

The ratio of the compound of the compound of formula (VI) to the salicylaldimine ligand used in step (ii) of variant B is preferably about 1:1.

In a preferred embodiment of the process according to the present invention $R_{o1}$ is a methyl group and $R_{o2}$ and $R_p$ are simultaneously hydrogen.

According to another preferred embodiment, $R_{o1}$ and $R_{o2}$ are methyl groups and $R_p$ is hydrogen.

According to another preferred embodiment, $R_{o1}$ and $R_{o2}$ are methyl and $R_p$ is methyl or bromide.

Still according to another preferred embodiment, $R_{o1}$ is methyl, $R_{o2}$ and $R_p$ are both hydrogen, $L_1$ is SIMes or IMes and $X_1$ is chloride.

Still according to another preferred embodiment, $R_{o1}$ and $R_{o2}$ are both methyl, $R_p$ is hydrogen, $L_1$ is SIMes or IMes and $X_1$ is chloride.

According to another preferred embodiment, $R_{o1}$ and $R_{o2}$ are both methyl, $R_p$ is bromide, $L_1$ is SIMes or IMes and $X_1$ is chloride. Still according to another preferred embodiment, $R_{o1}$ and $R_{o2}$ are both hydrogen, $R_p$ is tertbutyl, $S^2$ is methoxy, $L_1$ is SIMes and $X_1$ is chloride.

Still according to another preferred embodiment, $R_{o1}$ and $R_{o2}$ are both hydrogen, $R_p$ is tertbutyl, $S^3$ is methoxy, $L_1$ is SIMes and $X_1$ is chloride.

Thus, according to the present invention, the following catalysts can be prepared in a short, efficient and environmentally benign process avoiding the use of thallium salts:

Further, using the process according to the present invention, another subclass of ruthenium metathesis catalysts can be prepared, and preferred examples of this subclass are shown below:

The present invention is further illustrated by the following examples wherein manipulations of oxygen and moisture-sensitive materials were performed using Schlenk techniques under an argon atmosphere. THF, toluene, or hexane can be used as exemplary solvents.

General Procedure for the Preparation of Indenylidene-Schiff Base-Ruthenium Complexes The stoichiometric amounts of indenylidene first-generation catalyst (7), the corresponding Schiff base ligand, and silver(I) carbonate were added to a Schlenk flask (50-250 ml). The flask was evacuated and backfilled with argon. Dry THF (20 ml) was then transferred to the Schlenk flask (still under argon) and stirred for a period of 6-72 h. The reaction mixture was cooled at 0° C. whereas the white precipitate of $PCy_3AgCl$ (by-product) was removed by filtration. The filtrate was collected in a Schlenk flask (250 ml), and the solvent was removed by evaporation under reduced pressure.

Example 1

Complex 8 (Table 1; entry 22): Indenylidene first-generation catalyst (7) (500 mg, 0.54 mmol), 2-[(2-methylphenylimino)methyl]phenol (pKa: 8.93±0.35) (113 mg, 0.54 mmol), silver(I) carbonate (74.48 g, 0.27 mmol), and THF (10 ml) were reacted as described above for 72 h. The reaction mixture was investigated on $^1H$ and $^{31}P$ NMR, which revealed quantitative transformation to complex 8, namely 98%, of title complex.

$^1H$ NMR (in dichloromethane-$d_2$, 295 K)

(δ [ppm], multiplicity, intensity, J [Hz], assignment):

8.38 (d, [1H], J=7.4 Hz, H-22); 7.84 (d, [1H], J=7.0 Hz, H-7); 7.71 (d, [2H], J=7.4 Hz, H-25); 7.51 (t, [1H], J=7.1 Hz, H-27); 7.40 (d, [1H], J=7.5 Hz, H-19); 7.36 (dd, [2H], H-26); 7.30 (dd, [1H], H-12); 7.26-7.21 (unresolved multiplets, [5H]: H-4, H-21, H-9, H-10, H-11);

7.20 (d, [1H], J=8.8 Hz, H-5); 7.04 (d, [1H], J=8.8 Hz, H-2); 6.88 (s, [1H], H-16); 6.81 (dd, [1H], J=5.5 Hz, H-20); 6.50 (t, [1H], J=7.5 Hz, H-3); 2.52 (q, [3H], J=11.4 Hz, $PCy_3$); 2.42 (s, 3H, H-14); 1.95-1.54 (m, [20H], $CH_2$ of $PCy_3$); 1.30-1.23 (m, [20H], $CH_2$ of $PCy_3$).

$^{13}C$ NMR: 292.8 (b.s, C-15); 170.5 (s, C-1); 165.3 (s, C-7); 154.3 (s, C-8); 140.9 (s, C-18); 139.6 (s, C-17); 136.6 (d, C-16); 136.0 (s, C-2); 133.5 (s, C-4); 131.8 (s, C-23); 131.2 (s, C-13); 130.4 (s, C-13); 129.4 (s, C-12); 129.1 (s, C-19); 129.0 (s, C-26); 128.9 (C-9-11); 128.9 (s, C-21); 128.2 (s, C-22); 128.0 (s, C-27); 127.4 (s, C-24); 126.3 (s, C-25); 125.5 (C-9-11); 124.7 (s, C-20); 122.4 (s, C-5); 117.5 (s, C-6); 117.3 (C-9-11); 114.4 (s, C-3); 33.1 (s, C-14); cyclohexyl resonances: 33.1 (d, J=19.7 Hz); 29.8 (s); 29.3 (s); 27.8 (dd, $J^1$=30 Hz, $J^1$=10 Hz); 26.6 (dd, $J^1$=82 Hz, $J^1$=11 Hz); 26.5 (s).

$^{31}P$ NMR: 37.24 ppm (broad singlet)

FIGURE. Numbering scheme of ligands ($PCy_3$ omitted for clarity)

Structure Elucidation

The assignment of resonances in the $^1H$, $^{13}C$, and $^{31}P$ NMR spectra taken in dichloromethane-$d_2$ was performed using 1-D and 2-D homonuclear COSY and NOESY and HSQC and HMBC ($^1H$-$^{13}C$ and $^1H$-$^{31}P$) heteronuclear experiments.

The most characteristic features of the $^1H$ NMR spectrum in dichloromethane-$d_2$ is the presence of singlet resonance of indenylidene H-16 proton at 6.88 ppm (6.85 in $CDCl_3$), which has been assigned via heteronuclear long-range coupling with carbon C-15 in HMBC experiment. Interestingly the proton H-22 of indenylidene ligand (doublet at 8.38 ppm in $CD_2Cl_2$, 8.29 ppm in $CDCl_3$ and multiplet at 8.97 ppm in benzene-$d_6$) showed the same coupling with C-15. These allowed to assign the $^1H$ and $^{13}C$ signals of indenylidene part of the complex through homonuclear COSY/NOESY and heteronuclear HSQC/HMBC couplings.

The $^1H$ NMR spectrum of Schiff base ligand is more complicated due to overlapping of salicylidene proton as well as aromatic o-methylphenyl proton resonances in the 7.20-7.35 ppm region. Nevertheless, the doublet resonance of azomethine proton was found typically at 7.84 ppm, which was confirmed by heteronuclear $^1H$-$^{31}P$ HMBC experiment. The H-2 and H-3 resonances of salicylidene residue were fund considerably shifted up field as doublet and doublet of doublets at 7.04 and 6.50 ppm, respectively.

The $^{31}P$ NMR spectrum consists of broad singlet resonance at 37.24 ppm (37.12 and 37.66 ppm in $CDCl_3$ and in benzene-$d_6$, respectively).

The $^{13}C$ NMR spectrum in dichloromethane showed series of singlet resonances, except the C-15 and C-16 one, which were splitted into doublets.

Synthesis of Complex 10 (Following the Procedure Shown on Scheme 5)

A 50 ml dried Schlenk flask was charged with 1,3-bis(2,6-dimethylphenyl)-4,5-dihydroimidazolium tetrafluoroborate (0.8 g, 3.0 equiv.) and dry hexane 10 ml under an argon atmosphere. To this suspension was added LiHMDS (3.0 equiv.) at room temperature. The reaction mixture was stirred at 50° C. for 2 h, followed by filtration of this suspension to another 50 ml dried flask which contained complex 8 (0.5 g, 1.0 equiv.) under nitrogen. The reaction mixture was heated at 50° C. for 16 h, allowed to cool to room temperature. The brown-orange precipitate was then filtered, washed with hexane and dried in vacuo to give 10 as a dark brown microcrystalline solid in 81%.

Figure 6:
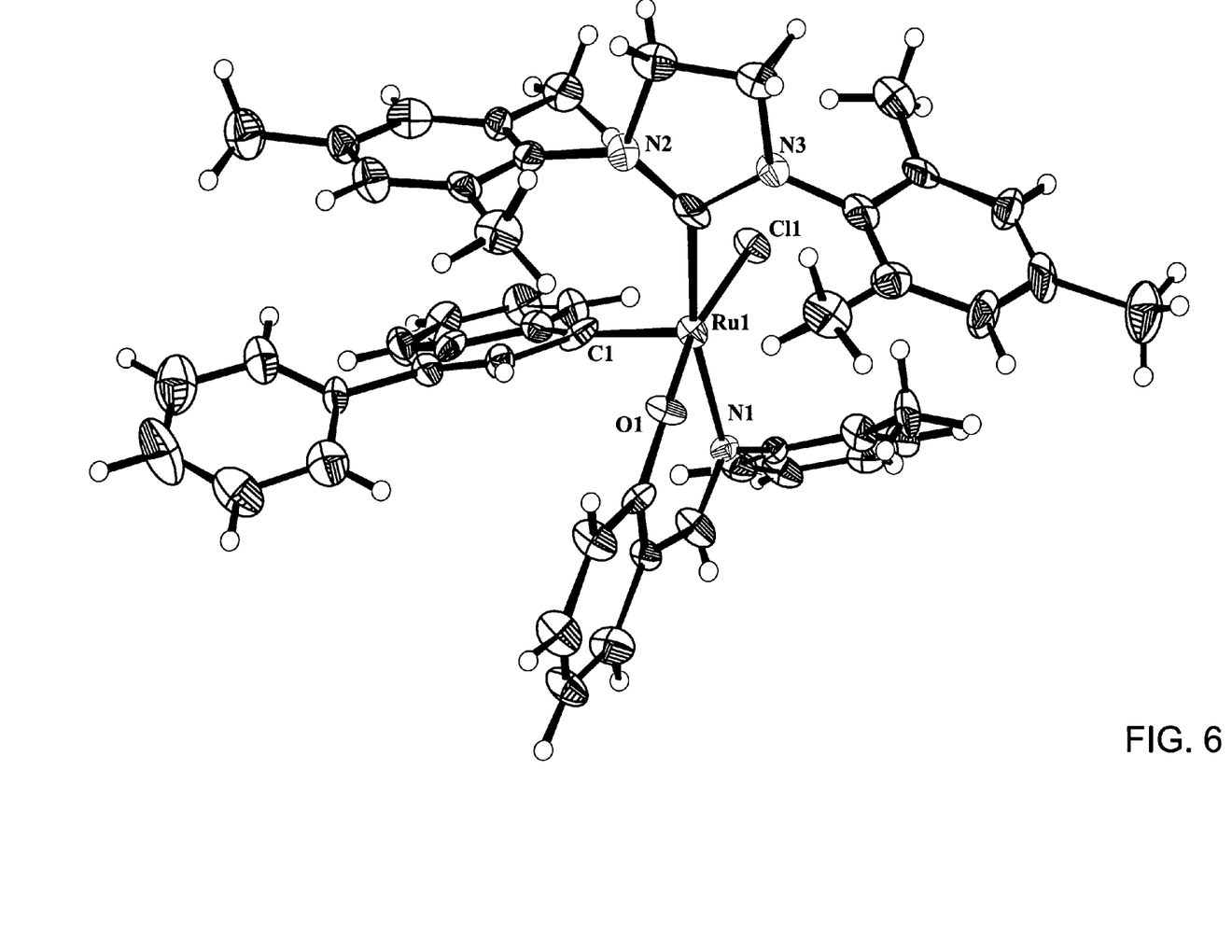
FIG. 6 is an image which shows the molecular structure of catalyst 10.

See FIG. 6. Molecular Structure of the Catalyst 10

Synthesis of Complex 11 (Following the Procedure Shown on Scheme 5)

A 50 ml dried Schlenk flask was charged with 1-cyclohexyl, 3-(2,6-dimethylphenyl)-4,5-dihydroimidazolium tetrafluoroborate (2.0 equiv.) and dry hexane 10 ml under an argon atmosphere. To this suspension was added LHMDSi (2.0 equiv.) at room temperature. The reaction mixture was stirred at 50° C. for 2 h, followed by filtration of this suspension to another 50 ml dried flask which contained complex 8 (0.5 g, 1.0 equiv.) under nitrogen. The reaction mixture was heated at 50° C. for 16 h, allowed to cool to room temperature. The orange-brown precipitate was then filtered, washed with hexane and dried in vacuo to give 11 as a orange brown microcrystalline solid. The crude product was purified by flash chromatography using mixture hexane/Et$_2$O. Yield 50%

Example 2

Complex 8.1 (Table 1; entry 13): Indenylidene first-generation catalyst (7) (500 mg, 0.54 mmol), 2-[(2,6-dimethylphenylimino)methyl]phenol (pKa: 8.93±0.35) (0.54 mmol), silver(I) carbonate (74.48 mg, 0.27 mmol), and THF (10 ml) were reacted as described above for 72 h. Yield (95%).

Example 3

Complex 8.2 (Table 1; entry 16): Indenylidene first-generation catalyst (7) (500 mg, 0.54 mmol), 2-[(4-Bromo-2,6-dimethylphenylimino)methyl]phenol (pKa: 8.69±0.35) (0.54 mmol), silver(I) carbonate (74.48 mg, 0.27 mmol), and THF (10 ml) were reacted as described above for 72 h. Yield (98%).

Example 4

Complex 8.3 (Table 1; entry 15): Indenylidene first-generation catalyst (7) (500 mg, 0.54 mmol), 2-[(4-methyl-2,6-dimethylphenylimino)methyl]phenol (pKa: 8.84±0.35) (0.54 mmol), silver(I) carbonate (74.48 mg, 0.27 mmol), and THF (10 ml) were reacted as described above for 72 h. Yield (98%).

Example 5

Complex 8.4 (Table 1; entry 17): Indenylidene first-generation catalyst (7) (500 mg, 0.54 mmol), 2-[(2,6-diisopropylphenylimino)methyl]phenol (pKa 8.83±0.35) (0.54 mmol), silver(I) carbonate (74.48 mg, 0.27 mmol), and THF (10 ml) were reacted as described above for 72 h. Yield (98%).

Example 6

Complex 8.5 (Table 1; entry 19): Indenylidene first-generation catalyst (7) (500 mg, 0.54 mmol), 2-[(phenylimino)methyl]phenol (pKa: 8.47±0.30) (0.54 mmol), silver (I) carbonate (74.48 mg, 0.27 mmol), and THF (10 ml) were reacted as described above for 72 h. Yield (92%).

Example 7

Complex 8.6 (Table 1; entry 21): Indenylidene first-generation catalyst (7) (500 mg, 0.54 mmol), 2-[(3-bromophenylimino)methyl]phenol (pKa: 8.76±0.35) (0.54 mmol), silver (I) carbonate (74.48 mg, 0.27 mmol), and THF (10 ml) were reacted as described above except for the reaction time (102 h). Obtained residue was than purified on chromatography colon. Yield (30%)

Example 8

Complex 8.6 (Table 1; entry 14): Indenylidene first-generation catalyst (7) (500 mg, 0.54 mmol), 2-[(2-chlorophenylimino)methyl]phenol (pKa: 8.58±0.35) (0.54 mmol), silver (I) carbonate (74.48 mg, 0.27 mmol), and THF (10 ml) were reacted as described above except for the reaction time (102 h). Obtained residue was than purified on chromatography colon. Yield (60%)

Example 9

Non-Working

Complex 8.7 (Table 1; entry 123): Indenylidene first-generation catalyst (7) (500 mg, 0.54 mmol), 2-[(4-tbutylphenylimino)methyl]-4-nitrophenol (pKa: 5.88±0.30) (0.54 mmol), silver (I) carbonate (74.48 mg, 0.27 mmol), and THF (10 ml) were reacted as described above except for the reaction time (6 h). The reaction mixture was investigated on $^{31}$P NMR, which did not reveal the presence of title complex.

Example 10

Not According to the Invention

Complex 8.8 (Table 1. Entry 118): Indenylidene first-generation catalyst (7) (500 mg, 0.54 mmol), 2-[(4-chlorophenylimino)methyl]-4-nitrophenol (pKa: 5.71±0.30) (0.54 mmol), silver (I) carbonate (74.48 mg, 0.27 mmol), and THF (10 ml) were reacted as described above except for the reaction time (24 h). The reaction mixture was investigated on $^{31}$P NMR, which did not reveal the presence of title complex.

Example 11

Not According to the Invention

Complex 8.8 (Table 1; entry 115): Indenylidene first-generation catalyst (7) (500 mg, 0.54 mmol), 2-[(4-methylphenylimino)methyl]-4-nitrophenol (pKa: 5.88±0.30) (0.54 mmol), silver (I) carbonate (74.48 mg, 0.27 mmol), and THF (10 ml) were reacted as described above except for the reaction time (24 h). The reaction mixture was investigated on $^{31}$P NMR, which did not reveal the presence of title complex.

Preparation of Benzylidene-Schiff Base-Ruthenium Complexes

Example 12

Complex A (Table 1; entry 13): Grubbs second generation catalyst (100 mg, 0.117 mmol), 2-[(2,6-dimethylphenylimino)methyl]phenol (pKa: 8.85±0.30) (0.117 mmol), silver (I) carbonate (16.27 mg, 0.058 mmol), and THF (2 ml) were reacted at room temperature during 2 h. The solvent was evaporated and crude reaction product purified on a chromatography column to give an orange-brown complex. Yield 22%.

Example 13

Complex B (Table 1; entry 15): Grubbs second generation catalyst (100 mg, 0.117 mmol), 2-[(2,4,6-trimethylphe- nylimino)methyl]phenol (pKa: 8.84±0.30) (0.117 mmol), silver (I) carbonate (16.27 mg, 0.058 mmol), and THF (2 ml) were reacted at room temperature during 2 h. The solvent was evaporated and crude reaction product purified on chromatography column to give an orange-brown complex. Yield 30%.

The invention claimed is:

1. A process for the preparation of a catalyst having the following formula:

(I)

wherein
$X_1$ denotes an anionic ligand;
$L_1$ is an N-heterocyclic carbene (NHC) ligand;
R' and R" are each independently hydrogen or a radical selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, aryl, arylidene, aryloxy, $C_{1-20}$ alkoxycarbonyl, $C_{1-8}$ alkylthio, $C_{1-20}$ alkylsulfonyl, $C_{1-20}$ alkylsulfinyl, $C_{1-20}$ alkylsulfonate, arylsulfonate, $C_{1-20}$ alkylphosphonate, arylphosphonate, $C_{1-20}$ alkylammonium and arylammonium, optionally substituted with one or more moieties selected from the group consisting of $C_{1-10}$ alkyl, $C_{1-10}$ alkoxy, and aryl, or R' and R" may together form an aryl, arylidene, cycloalkyl or heteroaryl group, benzylidene being excluded;
$S_1$ to $S_4$ may be the same or different and are defined as for the compound of formula (III) shown below;
A is heteroaryl, substituted or unsubstituted alkyl, heteroalkyl or cycloalkyl;
B is hydrogen, $C_1$-$C_{20}$ alkyl, $C_1$-$C_{20}$ heteroalkyl aryl or heteroaryl, wherein each non-hydrogen group may be optionally substituted with one or more moieties selected from the group consisting of $C_1$-$C_{10}$ alkyl and aryl;
$R_{o1}, R_{o2}, R_{m1}, R_{m2}$ and $R_p$ are each selected from the group consisting of hydrogen, $C_1$-$C_{20}$ alkyl, $C_1$-$C_{20}$ heteroalkyl $C_1$-$C_{20}$ alkoxy, aryl, aryloxy, heteroaryl, heterocyclolalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl, wherein $R_{o1}, R_{o2}, R_{m1}, R_{m2}$ and $R_p$ can be joined to form a fused cyclic aliphatic or aromatic ring optionally substituted with one or more moieties selected from the group consisting of $C_1$-$C_{20}$ alkyl, $C_1$-$C_{20}$ heteroalkyl, $C_1$-$C_{20}$ alkoxy, aryl, aryloxy, heteroaryl, heterocycloalkyl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl, comprising the following steps according to variant A or B:

variant A
(i) reacting a compound of the formula (II)

(II)

wherein $PL_1$ and $PL_2$ are the same or different and each denote a phosphine ligand, R' and R" are as defined above, and $X_1$ and $X_2$ may be the same or different and each denote an anionic ligand with a compound of the formula (III)

(III)

wherein A and B are as defined above and $S_1$ to $S_4$ are substituents which are selected such that the compound of the formula (III) has a $pK_a \geq 6.2$ in the presence of a weak base having a $pK_b$ in the range of 3.5-7.0 to obtain a compound of the formula (IV)

(IV)

wherein $PL_1$, $S_1$ to $S_4$, A, B, $X_1$, R' and R" are as defined above, (ii) reacting the compound of formula (IV) with a precursor of a non-phosphine neutral electron donor ligand to obtain catalyst (I) or variant B
(i) reacting a compound of the formula (V)

wherein $PL_1$, $PL_2$, $X_1$, $X_2$, R' and R'' are as defined above with a precursor of a non-phosphine ligand $L_1$ as defined above to obtain a compound of the formula (VI)

wherein $L_1$, $PL_2$, $X_1$, $X_2$, R' and R'' are as defined above, and
(ii) reacting the compound of formula (VI) with a compound of the formula (III)

wherein $S_1$ to $S_4$, A and B are as defined above, in the presence of a weak base having a $pK_b$ in the range of 3.5-7.0.

2. The process according to claim 1 wherein the weak base is selected from the group consisting of $Ag_2CO_3$, $CuCO_3$, $Li_2CO_3$, $Na_2CO_3$ and $K_2CO_3$.

3. The process according to claim 1 or 2 wherein the weak base is used in an amount of 1 to 2 equivalents relative to the amount of compound (III).

4. The process of claim 1 wherein in step (i) of variant A the compounds of the formulae (II) and (III), and the weak base are mixed and a solvent is added.

5. The process of claim 4 wherein the solvent has a dielectric constant $\geq 3$.

6. The process according to claim 5 wherein the solvent is selected from the group consisting of tetrahydrofuran, $CH_2Cl_2$, chloroform, diethyl ether and mixtures thereof.

7. The process according to claim 1 wherein $L_1$ is SIMes (N,N'-Bis(2,4,6-trimethylphenyl)imidazolinylidene) or IMes (N,N'-Bis(2,4,6-trimethylphenyl)imidazolylidene).

8. The process according to claim 1 wherein $X_1$ and/or $X_2$ is a halogen.

9. The process according to claim 1 wherein the substituents $S_1$ to $S_4$ are selected from the group consisting of hydrogen, amino, substituted or unsubstituted mono- and dialkylamino, $C_1$-$C_{20}$ alkyl, thioalkyl, aryl and aryloxy.

10. The process according to claim 9 wherein the substituents $S_1$ to $S_4$ are selected from the group consisting of hydrogen, methoxy, methylthio, amino, dimethylamino, trifluoromethyl, trifluoromethoxy, t-butyl, phenyl, phenoxy, chloro, bromo, piperidinyl, 1-pyrrolidino, 4-tert-butylphenoxy and 2-pyridyl.

11. The process according to claim 1 wherein $R_{o1}$, $R_{o2}$, $R_{m1}$, $R_{m2}$ and $R_p$ are selected from the group consisting of hydrogen, methyl, isopropyl, t-butyl, methoxy, dimethylamino and nitro.

12. The process according to claim 1 wherein the compound of formula (III) is a compound selected from the group consisting of compound Nos. 1 to 14 wherein B is hydrogen, A is and $S_1$ to $S_4$ and $R_{o1}$, $R_{o2}$, $R_{m1}$, $R_{m2}$ and $R_p$ are as defined below:

|  | Phenolic part | | | | Aniline part | | | | |
| --- | --- | --- | --- | --- | --- | --- | --- | --- | --- |
| Compound No. | $S^1$ | $S^2$ | $S^3$ | $S^4$ | $R_{o1}$ | $R_{o2}$ | $R_{m1}$ | $R_{m2}$ | $R_p$ |
| 1 | H | H | H | H | —CH₃ | H | H | H | H |
| 2 | H | H | OCH₃ | H | —CH₃ | H | H | H | H |
| 3 | H | OCH₃ | H | H | —CH₃ | H | H | H | H |
| 4 | H | H | OCH₃ | H | H | H | H | H | —ᵗBut |
| 5 | H | OCH₃ | H | H | H | H | H | H | —ᵗBut |
| 6 | —ᵗBut | H | —ᵗBut | H | —CH₃ | H | H | H | H |
| 7 | —ᵗBut | H | —ᵗBut | H | H | H | H | H | —ᵗBut |
| 8 | H | —ᵗBut | H | H | CH₃ | H | H | H | H |
| 9 | H | —ᵗBut | H | H | H | H | H | H | —ᵗBut |
| 10 | H | H | H | H | H | H | Br | H | H |
| 11 | H | H | H | H | H | H | H | H | —ᵗBut |
| 12 | H | OCH₃ | H | H | H | H | H | H | N(CH₃)₂ |
| 13 | H | H | OCH₃ | H | —CH₃ | —CH₃ | H | H | H |
| 14 | H | OCH₃ | H | H | —CH₃ | —CH₃ | H | H | H. |

13. The process according to claim 8 wherein the halogen is chloride.